(12) United States Patent
Bredno et al.

(10) Patent No.: US 10,438,381 B2
(45) Date of Patent: Oct. 8, 2019

(54) COMPUTER-IMPLEMENTED COMPOSITE TISSUE IMAGE WITH REAL-TIME ADJUSTABLE INTERFACE

(71) Applicant: Ventana Medical Systems, Inc., Tucson, AZ (US)

(72) Inventors: Joerg Bredno, San Francisco, CA (US); Srinivas Chukka, San Jose, CA (US)

(73) Assignee: Ventana Medical Systems, Inc., Tuscon, AZ (US)

( * ) Notice: Subject to any disclaimer, the term of this patent is extended or adjusted under 35 U.S.C. 154(b) by 0 days.

(21) Appl. No.: 15/970,574

(22) Filed: May 3, 2018

(65) Prior Publication Data

US 2018/0253871 A1    Sep. 6, 2018

Related U.S. Application Data

(63) Continuation of application No. PCT/EP2016/076351, filed on Nov. 2, 2016.
(Continued)

(51) Int. Cl.
   *G06K 9/00* (2006.01)
   *G06T 11/00* (2006.01)
   (Continued)

(52) U.S. Cl.
   CPC .......... *G06T 11/006* (2013.01); *G06T 7/0012* (2013.01); *G06T 7/174* (2017.01);
   (Continued)

(58) Field of Classification Search
   None
   See application file for complete search history.

(56) References Cited

U.S. PATENT DOCUMENTS

2002/0097920 A1 *   7/2002   Bender .............. H04N 5/23238
                                                            382/278
2006/0004275 A1     1/2006   Vija et al.
                             (Continued)

OTHER PUBLICATIONS

International Search Report and Written Opinion dated Jan. 31, 2017 in corresponding PCT/EP2016/076351 filed Nov. 2, 2016, pp. 1-14.
(Continued)

*Primary Examiner* — Stephen P Coleman
(74) *Attorney, Agent, or Firm* — Kilpatrick Townsend & Stockton LLP

(57) ABSTRACT

The disclosure relates to devices, systems and methods for generating a digital image of a tissue section that is a composite of two or more source digital images of adjacent tissue sections and which may have a real-time adjustable boundary between different source images. The devices include computer software products for a fused-view visualization tool which permits one or more of generating and displaying the composite image and modifying the location of one or more boundaries between source images comprising the composite image. The systems include computer-implemented systems such as work stations and networked computers for analyzing tissue samples using the fused-view visualization tool. The methods include processes for visualization of a tissue sample as a composite image derived from two or more slides of adjacent tissue sections, for example as an interactive composite image wherein the proportion of each source image in the composite image may be altered.

17 Claims, 14 Drawing Sheets
(7 of 14 Drawing Sheet(s) Filed in Color)

Related U.S. Application Data

(60) Provisional application No. 62/250,413, filed on Nov. 3, 2015.

(51) Int. Cl.
  *G06T 7/33* (2017.01)
  *G06T 7/174* (2017.01)
  *G16H 30/40* (2018.01)
  *G06T 7/00* (2017.01)

(52) U.S. Cl.
  CPC ............... *G06T 7/33* (2017.01); *G06T 11/00* (2013.01); *G06T 11/008* (2013.01); *G16H 30/40* (2018.01); *G06T 2207/10056* (2013.01); *G06T 2207/20012* (2013.01); *G06T 2207/20092* (2013.01); *G06T 2207/20221* (2013.01); *G06T 2207/30024* (2013.01)

(56) References Cited

U.S. PATENT DOCUMENTS

| | | | |
|---|---|---|---|
| 2012/0069049 A1 | 3/2012 | Howe et al. | |
| 2014/0378500 A1* | 12/2014 | Cohen | G01N 33/574 |
| | | | 514/291 |
| 2015/0310613 A1* | 10/2015 | Murakami | G02B 21/365 |
| | | | 382/128 |

OTHER PUBLICATIONS

Kwak et al, Multimodal Microscopy for Automated Histologic Microscopy for Automated Histologic Analysis of Prostate Cancer, BMC Cancer, Biomed Central, 2001, (16 pages), vol. 11, No. 62.

Malik, Muhammad Muddassir et al., Comparative Visualization for Parameter Studies of Dataset Series, IEEE Transactions, (2010), pp. 829-840, vol. 16 No. 5.

* cited by examiner

| | Thumbnail | Label | Block ID | Slide ID | | | | | |
|---|---|---|---|---|---|---|---|---|---|
| ☐ | | | TRSPZ003100 | TRSPZ003100-AP_FoxP3 | | ⬚ | ⓘ | ⊗ | ✎ |
| ☐ | | | TRSPZ003100 | TRSPZ003100-CD3SSRed | (3) | ⬚ | ⓘ | ⊗ | ✎ |
| ☐ | | | TRSPZ003100 | TRSPZ003100-CD4CD8 | | ⬚ | ⓘ | ⊗ | ✎ |
| ☐ | | | TRSPZ003100 | TRSPZ003100-CD4SS | | ⬚ | ⓘ | ⊗ | ✎ |
| ☐ | | | TRSPZ003100 | TRSPZ003100-CD8SS | | ⬚ | ⓘ | ⊗ | ✎ |
| ☐ | | | TRSPZ003100 | TRSPZ003100-D_CD20_L26_F | (1) | ⬚ | ⓘ | ⊗ | ✎ |
| ☐ | | | TRSPZ003100 | TRSPZ003100-HE | | ⬚ | ⓘ | ⊗ | ✎ |
| ☐ | | | TRSPZ003100 | TRSPZ003100-HE (2) | | ⬚ | ⓘ | ⊗ | ✎ |
| ☐ | | | TRSPZ003100 | TRSPZ003100-PerforinSS | (3) | ⬚ | ⓘ | ⊗ | ✎ |
| ☐ | | | TRSPZ003374 | TRSPZ003374-AP_FoxP3 | (1) | ⬚ | ⓘ | ⊗ | ✎ |
| ☐ | | | TRSPZ003374 | TRSPZ003374-CD3SSRed | | ⬚ | ⓘ | ⊗ | ✎ |
| ☐ | | | TRSPZ003374 | TRSPZ003374-CD4CD8 | (29) | ⬚ | ⓘ | ⊗ | ✎ |
| ☐ | | | TRSPZ003374 | TRSPZ003374-CD4SS | (2) | ⬚ | ⓘ | ⊗ | ✎ |

FIG.3

| | | | Block ID | Slide ID | | | |
|---|---|---|---|---|---|---|---|
| Viewer | | | | | | | |
| Register slides | | | TRSPZ003100 | TRSPZ003100-AP_FoxP3 | | 👁⊗✎ | |
| Run analysis | | | | | | | |
| ☑ | | ▓ | TRSPZ003100 | TRSPZ003100-CD3SSRed | (3) | 👁⊗✎ | |
| ☑ | | ▓ | TRSPZ003100 | TRSPZ003100-CD4CD8 | | 👁⊗✎ | |
| ☑ | | ▓ | TRSPZ003100 | TRSPZ003100-CD4SS | | 👁⊗✎ | |
| ☑ | | ▓ | TRSPZ003100 | TRSPZ003100-CD8SS | | 👁⊗✎ | |
| ☑ | | ▓ | TRSPZ003100 | TRSPZ003100-D_CD20_L26_F | (1) | 👁⊗✎ | |
| ☑ | | ▓ | TRSPZ003100 | TRSPZ003100-HE | | 👁⊗✎ | |
| ☑ | | ▓ | TRSPZ003100 | TRSPZ003100-HE (2) | | 👁⊗✎ | |
| ☑ | | ▓ | TRSPZ003100 | TRSPZ003100-PerforinSS | (3) | 👁⊗✎ | |
| ☐ | | ▓ | TRSPZ003374 | TRSPZ003374-AP_FoxP3 | (1) | 👁⊗✎ | |
| ☐ | | ▓ | TRSPZ003374 | TRSPZ003374-CD3SSRed | | 👁⊗✎ | |
| ☐ | | ▓ | TRSPZ003374 | TRSPZ003374-CD4CD8 | (29) | 👁⊗✎ | |
| ☐ | | ▓ | TRSPZ003374 | TRSPZ003374-CD4SS | (2) | 👁⊗✎ | |

FIG.4

COMPUTER-IMPLEMENTED COMPOSITE TISSUE IMAGE WITH REAL-TIME ADJUSTABLE INTERFACE

RELATED APPLICATIONS

This patent application is a continuation of International Patent Application No. PCT/EP2016/076351 filed Nov. 2, 2016, which claims priority to and the benefit of U.S. Provisional Application No. 62/250,413, filed Nov. 3, 2015. Each of the above patent applications is incorporated herein by reference as if set forth in its entirety.

FIELD

This specification relates, among other things, to devices, systems, and methods for manipulation and/or analysis of digitized images of tissue samples. This specification also relates to computer-implemented devices, systems and methods for viewing a composite image of two or more images from the same or different patients, animals, or other specimens, such as viewing a tissue sample as a composite image of two or more serial tissue section samples. The specification also relates to computer-implemented devices, systems and methods for comparing tissue specimens from the same or different patients, animals, or other specimens as a composite image having a real-time adjustable interface.

BACKGROUND

Digital Pathology refers to the management and interpretation of pathology information in a digital environment. Scanning devices are used to image slides of tissue sections, which may be stained, such that digital slides, e.g., whole slide images are generated. Digital Pathology software enables digital slides to be stored in a computer memory device, viewed on a computer monitor, and analyzed for pathology information. However, there are a number of impediments to the widespread adoption of Digital Pathology and the promise of its various benefits, such as imaging performance, scalability and management.

While certain novel features are shown and described below, some or all of which may be pointed out in the claims, the devices, systems and methods of this disclosure are not intended to be limited to the details specified, since a person of ordinary skill in the relevant art will understand that various omissions, modifications, substitutions and changes in the forms and details of the illustrated embodiments and in their operation may be made without departing in any way from the spirit of the disclosure. No feature described herein is critical or essential unless it is expressly stated as being "critical" or "essential."

SUMMARY

The present disclosure provides devices, systems and methods for the manipulation and/or analysis of digitized images of tissue samples. For example, in some embodiments, the present disclosure provides computer-implemented devices, systems and methods for visualizing a tissue sample as a composite digital image of two or more digital images. In further embodiments each composite digital image is generated from a glass slide using a different imaging mode (for example brightfield microscopy and fluorescence microscopy), or a glass slide in which a tissue section was prepared using a different stain (for example HE, IHC stains), or both, as compared to another of the two or more digital images.

In some embodiments, the process involves creating a single output digital image display of a tissue sample, which is a composite of two or more digital image files of adjacent tissue sections of the sample. In further embodiments, the two or more digital image files are from two to five digital image files. In some embodiments the two or more digital image files are two digital image files. In some embodiments, the digital image display is interactive, including an adjustable interface. In yet further embodiments, the digital image display comprises two or more regions, wherein each region has a size that can be modified by interaction with the display, and at least two of the regions show image data from a different adjacent tissue section. In yet further embodiments, interacting with the display to modify the single output digital image results in executing a local image registration process to match tissue structure along an interface between the modified regions. In some embodiments, the composite image is displayed in a side-by-side curtain view. In some embodiments, the composite image is displayed in an overlaid flashlight view.

In some embodiments, the disclosure provides an image analysis system including: 1) a processor, a memory containing instructions for execution by the processor, which if executed results in one or more of: a display of a digital composite image of a tissue section, wherein the composite image comprises two or more regions and each region ends at an adjustable boundary and is derived from image data from a different slide in a set of slides of adjacent tissue sections; a modification in size, shape or both of one or more regions; and, a modification in number of regions; 2) a client user interface for triggering the processor to execute the instructions; and, 3) a monitor which can display the client user interface, the one or more images of adjacent tissue sections, the results and combinations thereof. In some embodiments, the instructions for modifying the size, shape or both of a region are triggered by a user interacting with the display to move the adjustable boundary. In further embodiments, the instructions for modifying the size, shape or both of a region comprise a local image registration process.

In some embodiments, the disclosure provides a computer program product for visualizing a tissue sample, comprising: a tangible computer readable storage medium having a computer readable program code embedded therein, the computer readable program code is configured to: 1) produce and display an image of the tissue sample, which is a composite of one or more digital images in a set of digital images of adjacent tissue sections from the sample, wherein each of the one or more digital images comprises a proportion of the composite image and each digital image in the set of digital images of adjacent tissue sections is obtained using a different stain, a different imaging mode, or both; and, b) modify the proportion of one or more of the digital images in the composite image. In some embodiments, producing the composite image of the tissue sample, and/or modifying the proportion of one or more digital images in the composite image, comprises implementing local image registration at a boundary between digital images in the composite image.

Registration here refers to an image analysis step to align digital images of tissue sections. The goal of this step is to provide aligned digital images such that parts of tissue that were spatially close in a tissue block before creating tissue sections are close in the aligned digital images taken from sections from this tissue block. Many methods to register and align digital images are known to one skilled in the art, with one example implementation being described in the publication Sarkar A., Quan Yuan, and Chukka Srinivas, "A robust method for inter-marker whole slide registration of digital pathology images using lines based features," in Biomedical Imaging (ISBI), 2014 IEEE 11th International Symposium on, pp. 762-765. IEEE, 2014, which is incorporate herein by reference in its entirety. The present disclosure refers to two different kinds of registration. A global registration method aligns images by imposing a constraint that provides for identifying tissue sections that were close in the tissue block, and generating a whole image that reflects the closeness of the tissue sections in corresponding digital images. A local registration method finds a solution where this constraint is fulfilled best for a region of interest in the images. In some embodiments, the area of interest for local registration is an interface on a display that separates image data from two or more tissue sections presented next to each other.

In some embodiments, the disclosure provides a method for digitally viewing a tissue sample, which includes: 1) selecting a first image from a set of digital images of adjacent tissue sections, wherein each image is produced from a slide obtained using a different stain, a different imaging mode, or both; 2) selecting one or more second images from the set; 3) instructing a computer processor to execute instructions resulting in stacking and aligning the selected first image and one or more second images to form an aligned layer of images, if the images have not been registered before; it may further involve adjusting the position and orientation of one or more displayed images; 4) instructing the computer processor to execute instructions resulting in revealing a portion of one or more of the second images resulting in displaying a composite image of the tissue sample. In some embodiments, the method further comprises instructing the computer processor to execute instructions resulting in modifying the revealed portion of the one or more images. In some embodiments, instructing modifying involves moving a boundary displayed between adjacent images; and executing modification instructions involves executing a local image registration process to match tissue structure along a boundary between adjacent images.

While the disclosure provides certain specific embodiments, the invention is not limited to those embodiments. A person of ordinary skill will appreciate from the description herein that modifications can be made to the described embodiments and therefore that the specification is broader in scope than the described embodiments. All examples are therefore non-limiting.

BRIEF DESCRIPTION OF THE DRAWINGS

The patent or application file contains at least one drawing executed in color. Copies of this patent or patent application publication with color drawings will be provided to the Office upon request and the payment of the necessary fee.

FIG. 3 is a screenshot of a home screen comprised of interactive menu bars and windows, which home screen may be part of a windowed graphical client user interface associated with an embodiment of an image analysis program in accordance with this disclosure.

FIG. 4 is another screenshot of the home screen of FIG. 3 in which all slides from one tissue block are selected and a menu option, "Register Slides", is highlighted.

DETAILED DESCRIPTION

Figure 1:
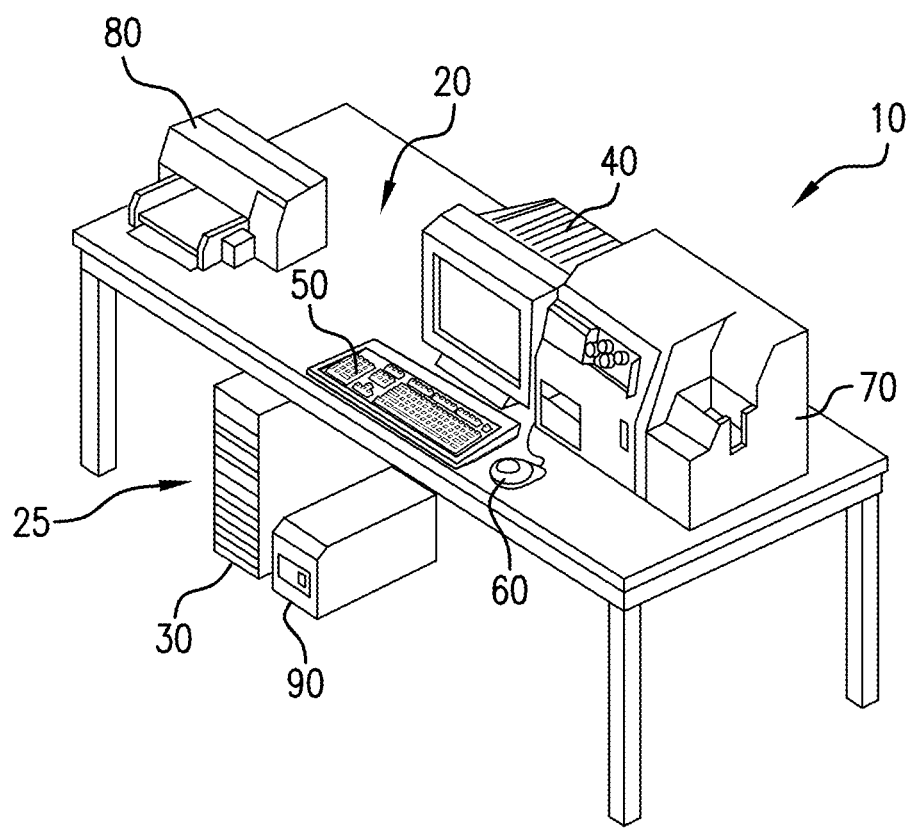
FIG. 1 is a perspective, pictorial representation of an embodiment of a medical imaging workstation system in which the devices, systems and methods according to this disclosure may be implemented.

Detailed descriptions of one or more embodiments are provided herein. It is to be understood, however, that the devices, systems and methods according to this disclosure may be embodied in various forms. Therefore, specific details disclosed herein are not to be interpreted as limiting, but rather as a representative basis for the claims and for teaching one skilled in the art to employ the present devices, systems and methods in any appropriate manner.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited.

The term "about" is meant to account for variations due to experimental error. All measurements or numbers are implicitly understood to be modified by the word about, even if the measurement or number is not explicitly modified by the word about.

The terms "comprising" and "including" and "having" and "involving" and the like are used interchangeably and have the same meaning. Similarly, "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Where ever the terms "a" or "an" are used, "one or more" is understood unless explicitly stated otherwise or such interpretation is nonsensical in context.

The terms "align" and "register" and all of their forms (for example, "aligning" and "registering") are used in the alternative and mean the same thing when used in connection with the term "image." For example, the phrases "aligned images" and "registered images" are used in the alternative to describe digital images, which have undergone an image registration process (for example a coarse registration and/or a fine registration process).

"Adjacent tissue sections of a tissue sample" refers to sections of a tissue sample, which have been prepared for use on a slide. In the context of this disclosure, adjacent tissue sections means only that the tissue section was taken from the same sample; it does not mean that the tissue sections necessarily abut one another. Thus, for example, if the disclosure refers to fusing together two digital images, one derived from a first tissue section and another derived from an adjacent tissue section or one derived from an adjacent tissue section and another derived from a second adjacent tissue section, only means that the two sections are derived from the same tissue sample, but not necessarily that the two sections abut one another in the tissue sample.

As is understood in the art, a digital image file comprises data (image data). Accordingly, references to digital images are also references to image data. For example, reference to a set of digital images implicitly discloses/refers to a set of image data comprising one or more image data files.

The analysis of pathology slides for diagnosis, therapy decision, and follow-up generally assesses the presence, shape, intensity and other features of the staining response of biological structures like cells, glands, tumors, etc. In many cases, information visible on one slide is not sufficient for a task at hand, and adjacent sections of tissue can be stained with different assays to interrogate multiple properties from the tissue. The information available from multiple slides stained with multiple assays is typically not used fully in an analysis of consecutive tissue sections because it is difficult and tedious for an observer to find, view, and analyze matching regions of tissue. In conventional microscopy, only one slide can be viewed at a time, and no tools are readily available to navigate to the same region and position on the tissue on different slides.

This disclosure relates to Digital Pathology, including devices, systems and methods for fused-view computer-implemented imaging. In some embodiments, the devices, systems and methods are implemented on a stand-alone workstation (which may include a modem for access to the internet). In some embodiments, the devices, systems and methods may be implemented over a computer network.

Two different assays and analysis problems for pathology data are used to exemplify and provide context to the fused-view digital imaging devices, systems and methods disclosed herein. In one embodiment, for the assessment of the immune response to a tumor, immune cells are stained with an IHC assay. For example, an assay comprising an anti-CD3 primary antibody stains T-lymphocytes and facilitates assessment of the occurrence of T-lymphocytes in a tumor, peritumoral stroma, or intratumoral stroma. For a more comprehensive analysis, one can assess if and how may such immune cells have infiltrated the tumor or surrounding structures. Typically, the immune cells are visible with the IHC stain, whereas tumor, intratumoral stroma, lymphatic vessels, etc. are better visible on slides stained with Hematoxylin and Eosin (H&E). Accordingly, one example involves fusion of a digital image derived from a slide prepared using a CD3-IHC stained tissue section with a digital image derived from a slide prepared using an H&E stained adjacent tissue section. In a second embodiment, for the assessment of the immune response to a tumor, PD-L1-positive immune cells are stained using a PD-L1/IHC assay. Because tumor cells can also carry the PD-L1 antibody, and it is desirable to also determine if the PD-L1 stained cell is a tumor cell or an immune cell, an H&E stain assay is used on an adjacent tissue section. Thus, the second example, involves fusion of a digital image derived from a slide prepared using a PD-L1/IHC stained tissue section with a digital image derived from a slide prepared using an H&E stained adjacent tissue section. However, although both examples involve one of CD3 and PD-L1 IHC staining combined with H&E staining, and both involve fusion of two slides, the disclosure encompasses fusion of digital images derived from multiple slides stained with different IHC and special stains assays, which may or may not also be combined with a digital image derived from an H&E stained slide.

Whether implemented on a stand-alone workstation or over a network, the systems according to this disclosure may include at least some of the following hardware components: a computer comprising an output device for displaying images and/or results such as a monitor and one or more input devices such as a keyboard and mouse or trackball for interacting with software programs, and a processor for executing the software programs. The systems may also include a storage device for storing sets of digital image files, wherein each set includes one or more whole slide images of adjacent tissue sections of the same tissue of a single patient. Each digital image file in a set may be generated from a glass slide using a different imaging mode (for example brightfield microscopy and fluorescent microscopy), or a glass slide in which a tissue section was prepared using a different stain (for example HE, IHC stains), or both, as compared to another digital image file in the set. The storage device can be part of the computer itself or it can be a separate device such as a network-accessible storage device. The systems may also include a scanner for producing the digital image files from glass slides.

In certain embodiments within the scope of this disclosure, a biological specimen (which may or may not be a tissue specimen) is placed on a substrate, which may or may not be a glass or microscope slide. In certain embodiments within the scope of this disclosure, the biological specimens (e.g., tissue specimens) that are imaged and compared may not originate from the same section or block of a patient. In certain embodiments within the scope of this disclosure, the digital images that are registered and available for use in accordance with methods within the scope of this disclosure may be images of non-adjacent tissue sections from a single patient. In certain embodiments within the scope of this disclosure, the digital images that are registered and available for use in accordance with methods within the scope of this disclosure may be images of biological specimens from different patients. In certain embodiments within the scope of this disclosure, the system may be used to compare tissue specimens from the same or different patients, animals, or other specimens. One example for such an embodiment would allow to view and compare normal and diseased tissue or tissue at different stages of a disease process side by side while matching of the underlying anatomy of the viewed tissue blocks.

Whether implemented on a stand-alone workstation or over a network, the systems may also include the following software components: an image analysis program comprising an image registration module and a fused-view imaging module (which itself may include an optional local registration module, as well as an optional global registration module (having a coarse registration module and/or a fine registration module).

The fused-view imaging module, when executed by the processor, results in an image of a tissue sample, which is a composite of two or more selected digital images, which have been registered, wherein each of the selected digital images is derived from a different adjacent tissue section of a tissue sample. In other words, different regions of the composite image show image data from different digital adjacent tissue section slide images. The fused-view imaging module further enables a user to determine and manipulate which regions on the composite image contain data from which of the selected digital images using a client user interface. In one possible embodiment, two or more registered fields of view (FOVs) of the same size as the displayed combined image are obtained as regions from the two or more digital tissue images. The selected regions can contain a subset of the image information, or they can be the digital images in their entirety. Regions are assigned to the display area to show image content from the first, the second, or any other of the FOV images. The assignment of these regions to the display area can be interactively modified by a user using input devices and by interacting with the displayed image. In some of the embodiments, the display is updated in real-time whenever the user changes the assignment of regions. For example, in some embodiments, the client user interface is implemented in a "curtain view" wherein a slider is provided at the boundary of adjacent regions; the slider enables a user to increase the proportion of image data provided to the composite image from one of the selected images while simultaneously decreasing the proportion of image data provided to the composite image from the abutting digital image. In another or further example, the client user interface is implemented in a "flashlight view" wherein a portion of the digital image is "illuminated" in, for example, a disc shape, to provide image data from a secondary, selected digital within the disc shape and leaving image data from the main, selected digital image outside the disc shape. For this embodiment, the region assigned to a second image in the combined display is disk-shaped, and the position and size of this disk can be adjusted by a user of the system. However the region is not limited to being disk-shaped but could be any other desired shape such as rectangular or square. The illuminated area may be enlarged, decreased, and/or moved around the image to select which portion of the image is derived from a secondary, selected slide rather than the main, selected slide. Also for this example, user interaction modifies the respective assignment of the disk-shaped region in the displayed area.

The "global" registration module, when executed by the processor, results in aligning at least two digital images in a set of digital images of adjacent tissue sections thereby creating a set of aligned digital images. Registration can be accomplished by any means known in the art, for example as described in PCT App. No. PCT/EP2014/054781, filed Mar. 12, 2014, entitled "Whole Slide Image Registration and Cross-Image Annotation Devices, Systems and Methods," which is herein incorporated by reference in its entirety.

The optional "local" registration process within the fused-view imaging module, operates on a fused-view image to align two or more digital images, which make up the fused-view image, along an interface between the two or more digital images when the interface is adjusted. For example, in embodiments wherein a slider denoting the interface between adjacent images is moved to expand the view of one image at the expense of another image, the overlay between the two images may be imperfect due to the fact that the images are derived from adjacent sections and may not be identical. Local registration is intended to minimize or reduce visual artifacts at the boundary of the overlaid region, for example, by matching tissue structure along the boundary region. For the curtain view, the flashlight view, as well as for other embodiments of this invention, interface regions are defined as those areas in the displayed image where the assignment of regions to the display changes. The process of local registration modifies the position and/or orientation of one or more of the displayed FOVs such that the image content from two or more FOVs displayed in this interface region is as similar as possible. Local registration can be implemented by determining the image transformation, for example translation and rotation of one of the images that maximizes a quantitative measure of image similarity in the interface area. For example, the correlation of two or more FOV images in the interface region can be used as similarity measure. It will be evident to one skilled in the art that many different types of image transformations and many different measures of image similarity can be used to achieve this task.

In some embodiments, the computer-implemented methods also comprise: a computer-implemented "global" registration process for aligning at least two digital images from the same tissue block, section, or sample of a single patient resulting in a set of aligned digital images, wherein each digital image in the set may be derived from an image obtained using a different stain, a different imaging mode, or both as compared to the other digital images in the set. In some embodiments of this invention, the global image registration step is used to select FOVs from different tissue images that show the same tissue region, while local registration is applied to the FOV images to improve the similarity of displayed tissue in the interface regions of the combined display.

Although examples described herein refer to digital imaging of slides prepared using certain staining or imaging methods, the specification is not limited to those staining or imaging methods but encompasses digital imaging of all possible slide preparations. Further, although the examples described herein describe a particular image as the main image (for example an H&E image) and another image is a secondary image (e.g. an IHC stain), the specification is also not limited to those contexts. For example, the IHC stain may be primary and the H&E secondary in certain embodiments. Also, although the examples describe "curtain" and "flashlight" views, again the specification is not limited to those imaging modes but encompasses all possible methods of analyzing fused view images by viewing image data from one digital image in one region of the composite image and viewing image data from one or more additional digital images in other regions of the slide. In other words, the specification is directed generically at visualizing information derived from any two or more slides of a tissue sample in a single composite image of the tissue sample rather than the typical side-by-side viewing of two images of the tissue sample, offering functionality for the analysis of tissue stained with multiple assays on multiple slides, that is not available or is different than the typical side-by-side viewing approach.

Referring now to the Figures, wherein like reference numerals refer to like parts throughout, FIG. 1 is a perspective, pictorial representation of an embodiment of a medical imaging workstation system 10 in which the devices, systems and methods according to this disclosure may be implemented. As shown, the medical imaging workstation system 10 includes a computer 20 having a housing for hardware components 30 such as a processor ("CPU") (not shown), a storage device (not shown), a graphics processor unit ("GPU") (not shown), and optionally a modem (not shown); a first output device, which in the illustrated example is a monitor 40; a first user input device, which in the illustrated example is a keyboard 50; and, a second user input device, which in the illustrated example is a pointing device for interacting with the display such as a track ball or mouse 60. As is known in the art, although the computer 20, hardware component 30, monitor 40, and user input devices 50, 60 are illustrated as separate components, they may be integrated in fewer parts such as they may all be integrated in the form of a laptop computer. The medical imaging workstation system 10 may also include additional peripherals such as a third input device, which in the illustrated example is a slide scanner 70, a second output device, which in the illustrated example is a printer 80, a back-up power supply 90, and external storage devices (not shown), among other devices which are known to be associated with computer-implemented medical imaging systems. In some embodiments, the medical imaging workstation system 10 may include more than one monitor 40 for ease of simultaneous viewing of multiple digital tissue images on multiple screens. As a person of skill appreciates, the specific components may change as technology changes. For example, a peripheral pointing device may not be necessary if the screen is responsive to a user's finger, or voice commands.

The medical imaging workstation system 10 also includes software components such as an image analysis program comprising a fused-view imaging module including a local registration module, and optionally a global registration module. The software components may be one or more files, which are stored on the storage device (for example the software components may be stored on an internal hard drive) and/or the software components may be stored on a memory disc such as a DVD, CD or memory card, which can be accessed by the processor when the memory disc is inserted into the housing 30 through a memory-disc receiving port 25.

The CPU is operatively connected to the various peripherals and hardware components, including the storage device and the GPU. The storage device may temporarily or permanently store sets of digital images, which may be imported into the system, for example by a scanning device. The sets of digital images include one or more digital images of adjacent tissue sections of a single patient, wherein each image can be obtained using a different stain/label/marker, a different imaging mode, or both as compared to another image. The GPU processes instructions from an image display program and image analysis program (which may be combined in a single program). When executed, for example by the GPU, the image display program may provide a windowed graphical user interface ("GUI") on the monitor 40 with multiple windows such that a user may interact with the GUI to provide instructions resulting in a processor, such as for example the CPU, executing one or more aspects of the image analysis program, and/or may result in displaying one or more of the stored digital images on one or more of the monitors 40, either in their native (originally-scanned) format or as modified by the image analysis program. As previously mentioned, the image analysis program may comprise a registration module and fused-view imaging module. When executed, for example by the CPU, the registration module results in aligning a least two of the stored digital images, even stored digital images that are obtained using different stains, different imaging modes, or both creating a set of aligned images. When executed, for example by the CPU, the fused-view imaging module results in displaying an image of a tissue sample, which is comprised of two or more digital images derived from slides of adjacent tissue sections and which image can be modified to change which portions of the composite image are derived from one digital image versus another.

Figure 14:
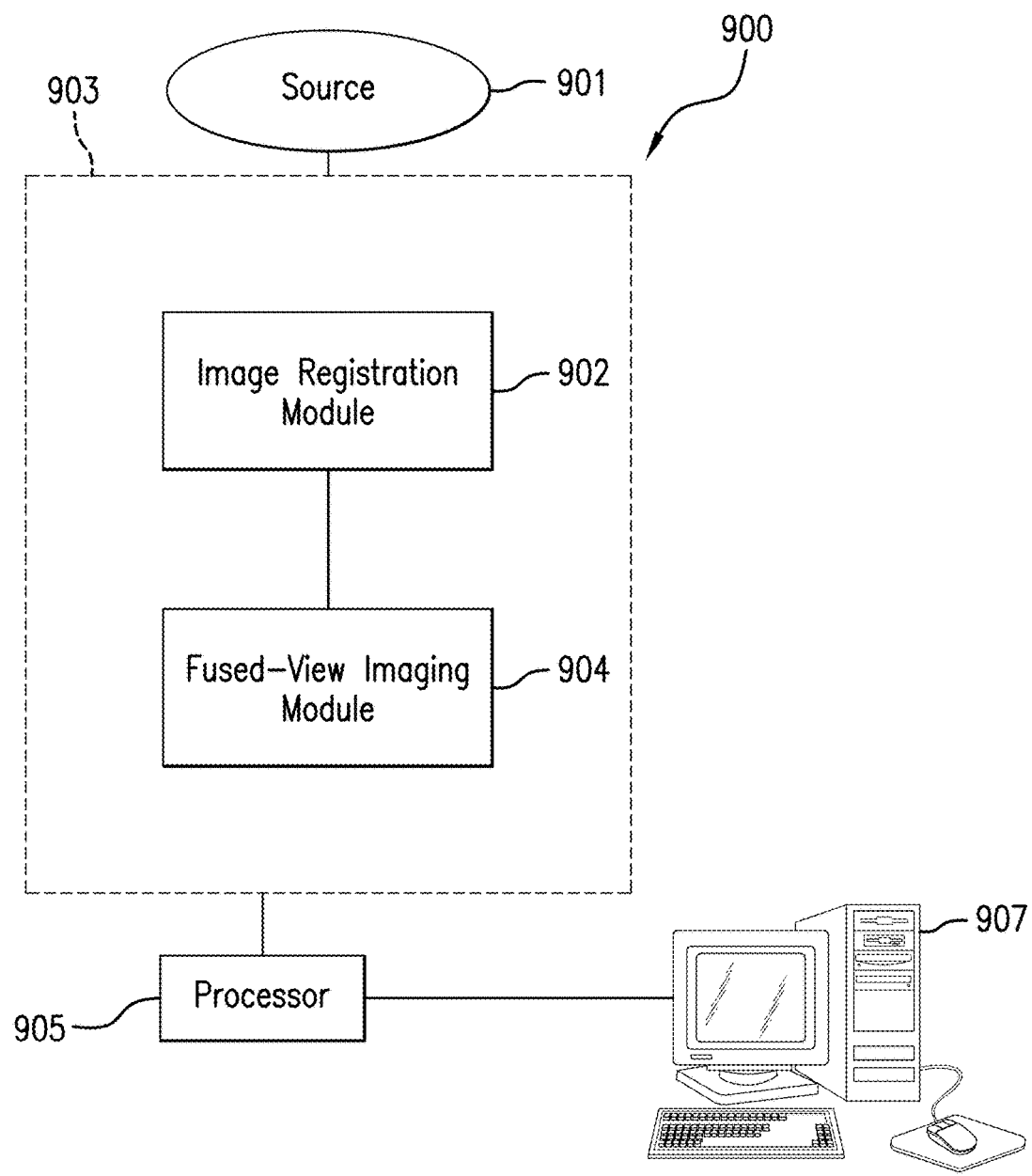
FIG. 14 is a flow diagram illustrating an embodiment of a method carried out by an image analysis software program in accordance with this disclosure.

FIG. 14 illustrates a system 900, for example, an imaging system for image analysis in accordance with an exemplary embodiment of the present subject invention. System 900 comprises a source 901 for generating a multi-channel image or multi-channel image data (for example, an RGB image or RGB image data and/or a multispectral image or multispectral image data). For instance, source 901 may be or include a fluorescence microscope, camera, optical, scanner, CCD, or imaging system that generates a fluorescent image, or a bright-field microscope, camera, optical scanner, or imaging system generating an RGB image, multispectral image, and/or RGB or multispectral image data. Examples of imaging systems can be, for example, any fluorescent or a brightfield microscope with spectral filter wheel or a whole slide scanner. Source 901 is in communication with a memory 903, which includes a plurality of processing modules or logical operations that are executed by processor 905 coupled to computer interface 907. For instance, a sample, such as a biological specimen, may be mounted on a slide or other substrate or device for purposes of imaging by a microscope, camera, scanner, CCD, or other optical system coupled to memory 903, with analysis of images of the specimen being performed by processor 905 executing one or more of the plurality of modules stored on memory 903 in accordance with the present disclosure. The analysis may be for purposes of identification and study of the specimen. For instance, a biological or pathological system may study the specimen for biological information, such as the presence of proteins, protein fragments or other markers indicative of cancer or other disease, or for other purposes such as genomic DNA detection, messenger RNA detection, protein detection, detection of viruses, detection of genes, or other.

The specimen, for example, a tissue specimen or cytology specimen may be stained by means of application of one or more different stains that may contain one or more different quantum dots, fluorophore(s), or other stains. For example, in a fluorescent slide, the different stains may correspond to different quantum dots and/or fluorophores. The fluorophores may comprise one or more nano-crystalline semiconductor fluorophores (e.g., quantum dots), each producing a peak luminescent response in a different range of wavelengths. Quantum dots are well known, and may be commercially available from Invitrogen Corp., Evident Technologies, and others. For example, the specimen may be treated with several different quantum dots, which respectively produce a peak luminescent response at 565, 585, 605, and 655 nm. One or more of the fluorophores applied to the specimen may be organic fluorophores 14 (e.g., DAPI, Texas Red), which are well known in the art, and are described in at least commonly-owned and assigned U.S. Pat. No. 8,290, 236, the contents of which are incorporated by reference herein in their entirety. Moreover, a typical specimen is processed utilizing a staining/assay platform, which may be automated, that applies a stain, for example, a stain containing quantum dots and/or organic fluorophores to the specimen. There are a variety of commercial products on the market suitable for use as the staining/assay platform.

After preliminary tissue processing and staining, one or more digital images of the specimen may be captured at source 901 via, for instance, a scanner, CCD array spectral camera, or other imaging system that is used for imaging a slide containing a sample of a material, and generate a digital image of the sample on the slide. (In accordance with the present invention, fused images comprise portions of at least two different slides.) The slide containing the sample is subjected to a light source for illuminating the specimen at wavelengths intended to produce a luminescent response from the stain applied to the specimen. In the case of quantum dots, the light source may be a broad spectrum light source. Alternatively, the light source may comprise a narrow band light source such as a laser. An RGB brightfield image may also be captured. The imaging system may include, for example, a digital camera, a microscope or other optical system having one or more objective lenses, and light sources, as well as a set of spectral filters. Other techniques for capturing images at different wavelengths may be used. Camera platforms suitable for imaging stained biological specimens are known in the art and commercially available from companies such as Zeiss, Canon, Applied Spectral Imaging, and others, and such platforms are readily adaptable for use in the system, methods and apparatus of this subject disclosure. The image may be supplied to memory, or storage device 903, either via a wireless or wireline connection, for example, a cable connection between the source 901 and computer 907, via a computer network, or using any other medium that is commonly used to transfer digital information between computers. The image may also be supplied over the network to a network server or database for storage and later retrieval by computer 907. Besides processor 905 and memory 903, computer 907 also includes user input and output devices such as a keyboard, mouse, stylus, and a display/touchscreen. As will be explained in the following discussion, processor 905 executes modules stored on memory 903, performing analysis of the image, of the image or image data derived from such images, quantitative analysis, and display of quantitative/graphical results to a user operating computer 907.

Modules stored on memory 903 may include an image registration module 902 and a fused-view imaging module 904 as described above and further herein. However, the operations performed by these modules are not limited to those described herein, and the sequence, arrangement, and total number of modules may vary, with the presently described embodiment being solely for example purposes.

The software modules may be accessed via a client user interface, for example, a user interface associated with computer 907.

Once the program is launched, a user may select a digital image 921 for analysis. In the embodiment described herein, the user selects images from a series of images of adjacent serial sections, wherein, for example, at least one of the sections has been stained with H&E and other sections have been stained with one or more different IHC stains. However, the invention is not limited to fuse-view imaging of adjacent serial sections. For example, in other embodiments a viewer could select from images of tissue specimens from the same or different patients, animals, or other specimens in order to view and compare, for example, normal and diseased tissue or tissue at different stages of a disease process.

Through the client interface, a user may then invoke the image registration module 902, which when executed for example by the CPU or processor 905, aligns the selected images, for example by matching of the underlying anatomy of the viewed tissue blocks.

Through the client interface, a user may also invoke the fused-view imaging module 904, which when executed, for example by the CPU or processor 905, generates a fused image of selected images 921 which were registered by the image registration module. For example, the fused-view imaging module 904 may generate a composite image of the selected registered slides in a side-by-side "curtain" view (including one or more curtains) and/or in a "flashlight" view wherein one or more portions of one or more secondary slides appear to replace one or more portions within a primary slide.

Figure 2:
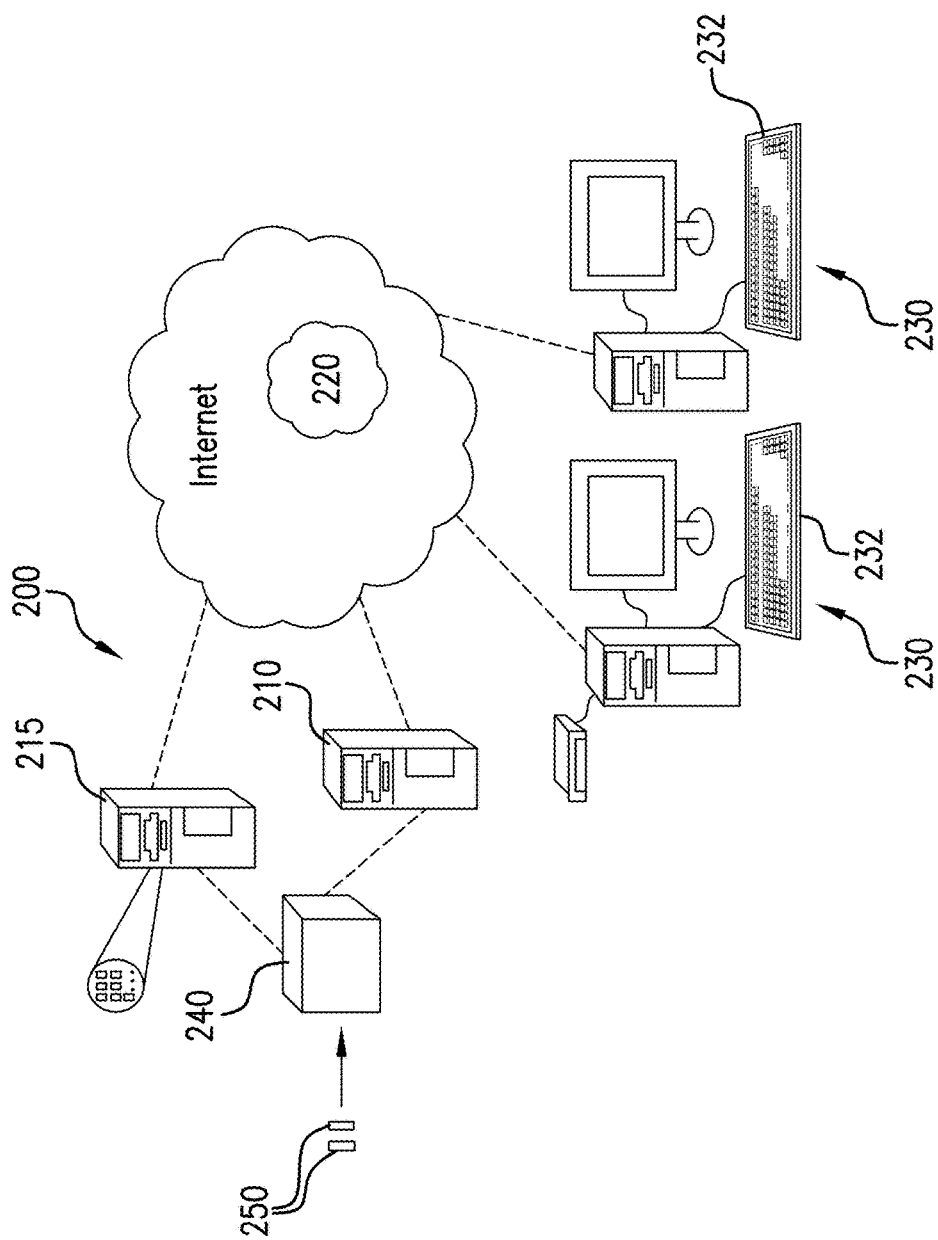
FIG. 2 is a network diagram illustrating an embodiment of a networked system in which the devices, systems and methods according to this disclosure may be implemented.

FIG. 2 is a network diagram illustrating an embodiment of a networked system in which the devices, systems and methods according to this disclosure may be implemented. As shown, the system 200 includes a database server 210 and a network-accessible storage device 215, each of which is connected to a network 220. The storage device 215 stores sets of digital images, wherein each set includes one or more digital images of adjacent tissue sections of a single patient. Each image in a set may be obtained by using a different stain, a different imaging mode or both as compared to another image in a set. One or more client computers 230, which may have associated input and output devices such as a keyboard 232, mouse (not shown) and printer (not shown) are also connected to the network 220 by any means known in the art (for example a dedicated connection, a DSL or cable modem, a wireless internet connection, a dial-up modem or the like). The client computer 230 includes a web browser, which is used to access the digital images in the stored device 215. In exemplary embodiments of the present invention, cloud storage may be utilized for storing the digital images.

The client computer 230 includes at least one processor configured to execute instructions relating to an image analysis program. The image analysis program may be downloaded to the client computer 230 from the server 210. The image analysis program may include an image viewer module, which provides a client user interface such that when executed, the image viewer module may provide a windowed GUI (and may include multiple windows) that enables a user to provide instructions resulting in the processor executing one or more aspects of the image analysis program and/or may result in displaying one or more of the stored digital images, either in their originally-scanned format or as modified by the image analysis program. If the stored images have not previously been registered (or if a user desires to use a second or different registration methodology), the image analysis program may optionally enable a user to select images for registration from a set of images obtained from a tissue section of a single patient, but wherein at least some of the images in the set may have been made using a different stain, or a different mode or both as compared to other images in the set. The image analysis program also enables a user to view a digital image of the tissue sample that is a composite of two or more digital images in the set of digital images. In some embodiments, the system 200 also includes a scanner 240 for scanning whole slides 250 and producing the digital images, which are stored in the storage device 215.

As a person of skill understands, implementing the image analysis program in the context of a computerized network enables certain activities that may otherwise be limited by stand-alone work stations. For example, pathologists who are not co-located, and indeed may be remote from one another, may collaborate in analyzing images, or the right pathologist may be reached at the right time, independent of location.

FIGS. 1 and 2 illustrate certain elements, which may be present in one or more computer system or network topologies. A person of skill understands that computer systems and networks in which devices and systems according to this disclosure may be implemented may encompass other computer system and network topologies, and may include more or less elements in those other computer system and network topologies. In other words, the embodiments of FIGS. 1 and 2 are not limiting. For example, in some embodiments, cloud storage may be used for storing the digital images.

Accordingly, an exemplary embodiment of a computer system for use in accordance with the present disclosure may include any number of computer platforms or multiple types of computer platforms, such as workstations, personal computers, servers, hand-held devices, multi-processor systems, microprocessor-based or programmable consumer electronics, network PCs, minicomputers, mainframe computers or any other present or future computer.

An exemplary embodiment may also be practiced in distributed computing environments where tasks are performed by local and/or remote processing devices that are connected (by, for example, hardwired connections, wireless connections, or a combination thereof), in a communications network. In a distributed computing environment, program modules may be located in both local and remote computer storage media including memory storage devices. It will, however, be appreciated by one of ordinary skill in the art that the aforementioned computer platforms as described herein are specifically configured to perform the specialized operations of the described invention and are not considered general purpose computers.

Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Examples of input devices include a keyboard, cursor control devices (e.g., a mouse), a microphone, a scanner, and so forth.

Examples of output devices include a display device (e.g., a monitor or projector), speakers, a printer, a network card, and so forth. Display devices may include display devices that provide visual information, this information typically may be logically and/or physically organized as an array of pixels.

An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework. Those of ordinary skill in the related art will appreciate that interfaces may include one or more GUI's, CLI's or a combination thereof.

A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows-type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer-readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. 가 μ가 μå now in use or that may later be developed, may be considered a computer program product.

As will be appreciated, these program storage media typically store a computer software program and/or data. Computer software programs, also called computer control logic, typically are stored in system memory and/or the program storage device used in conjunction with memory storage device. In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote.

In the presently described embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution.

Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems.

Figure 5:
FIG. 5 is another screenshot of the home screen of FIG. 3 with yet another menu option, "Viewer", highlighted.

FIGS. 3-5 together illustrate an embodiment of the client user interface for interacting with the processor to view images in a fused view format. In the illustrated embodiment, the client user interface is implemented over two basic tools based on which the fused-view imaging framework is presented. A first software tool (FIG. 3) presents a list of available tissue images, typically grouped together by the tissue block from which the tissue section was obtained. Slides can be selected in this list and actions like a global registration or a viewing of the slides can be triggered. For example, as shown in FIG. 4, all slides from one tissue block (i.e., the Block Id is the same for each image) are selected and a menu option, "Register Slides", is highlighted and/or selected. As another example, and as shown in FIG. 5, certain registered slides from a tissue block are selected and a different menu option, "Viewer", is highlighted and/or selected. A second software tool (FIGS. 7-13) provides the viewing functionality further disclosed in this disclosure. The functionalities provided in this disclosure, however, can be integrated with other annotation/viewer GUI tools and other image analysis/management tools. For example, any whole slide viewer may be used to implement the products and methods of the disclosure including Ventana ImageViewer, Ventana VIRTUOSO Viewer and Ventana VECTOR viewer.

Figure 7:
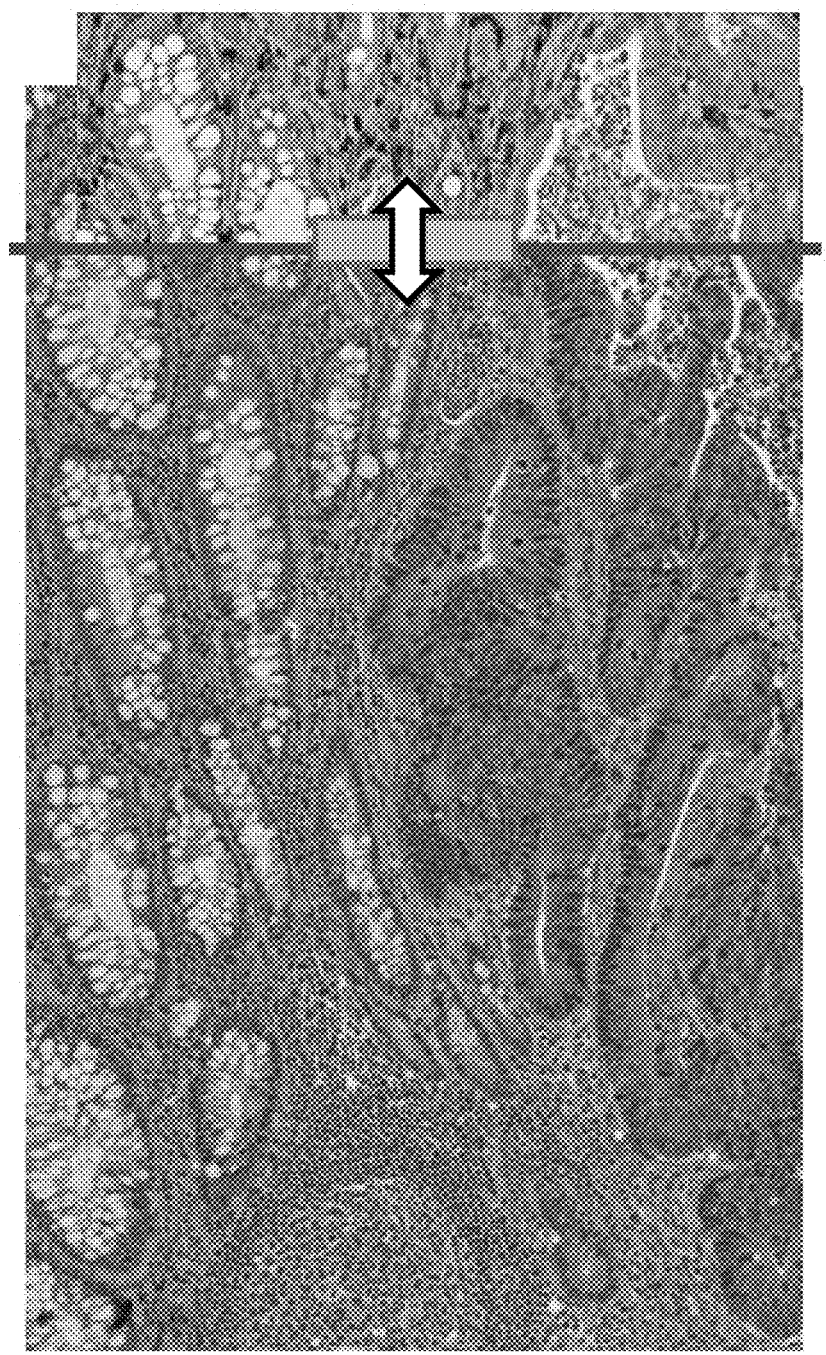
FIG. 7 is a screenshot of an embodiment of the fused-view module GUI in which two or more digital slides may be viewed in a curtain-view composite image, and which may be launched from the home screen of FIG. 3.

Also illustrated in FIG. 7, for example, the Viewer GUI includes a "Viewer" window 326 having a menu bar and a number of icons to facilitate a user's interaction with the displayed image (such as zoom buttons 340 and pan button 350). Included among the viewing tools are fused-view visualization buttons such as curtain-view mode 360 and flashlight mode 370.

Figure 8:
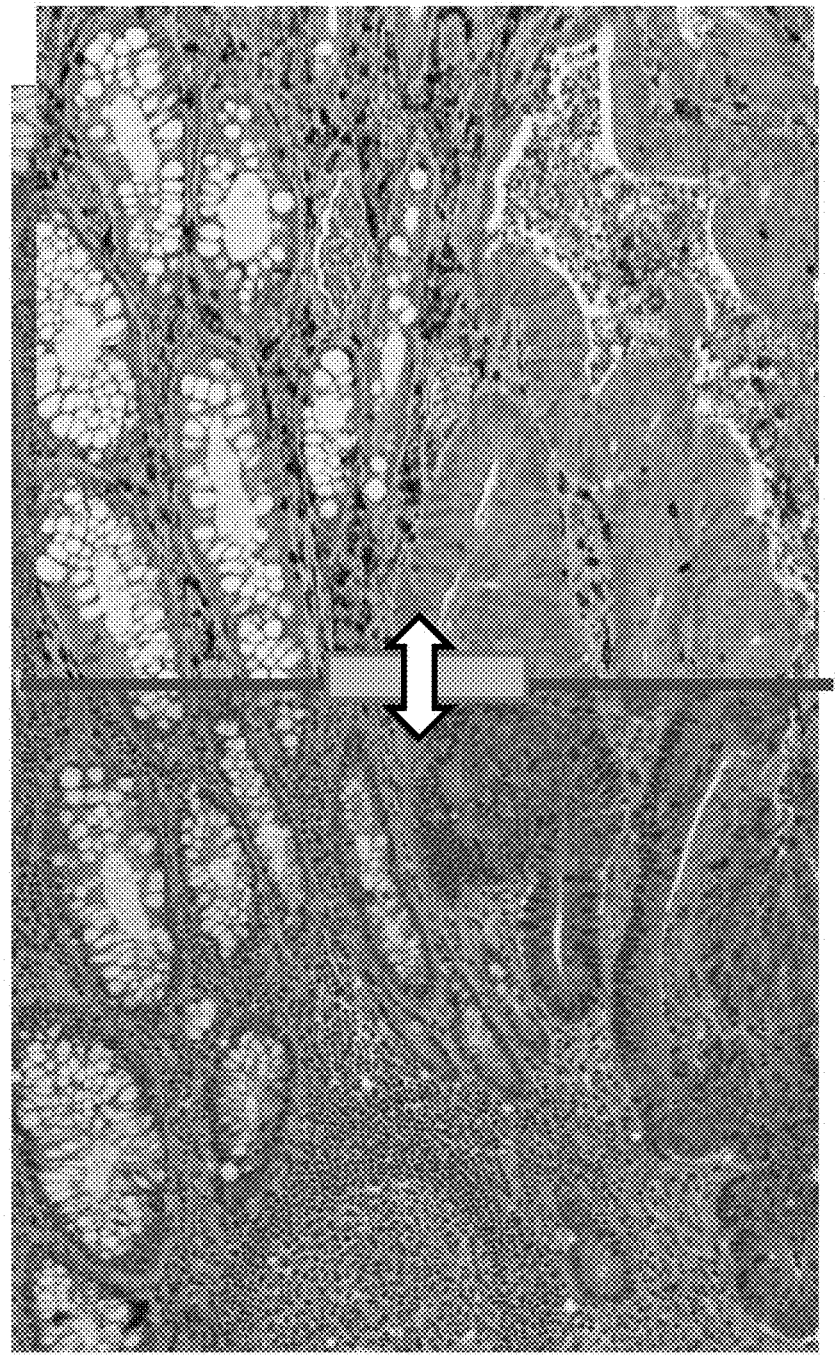
FIG. 8 is another screenshot of the fused-view module GUI of FIG. 7 after the boundary between different digital images has been moved.
Figure 9:
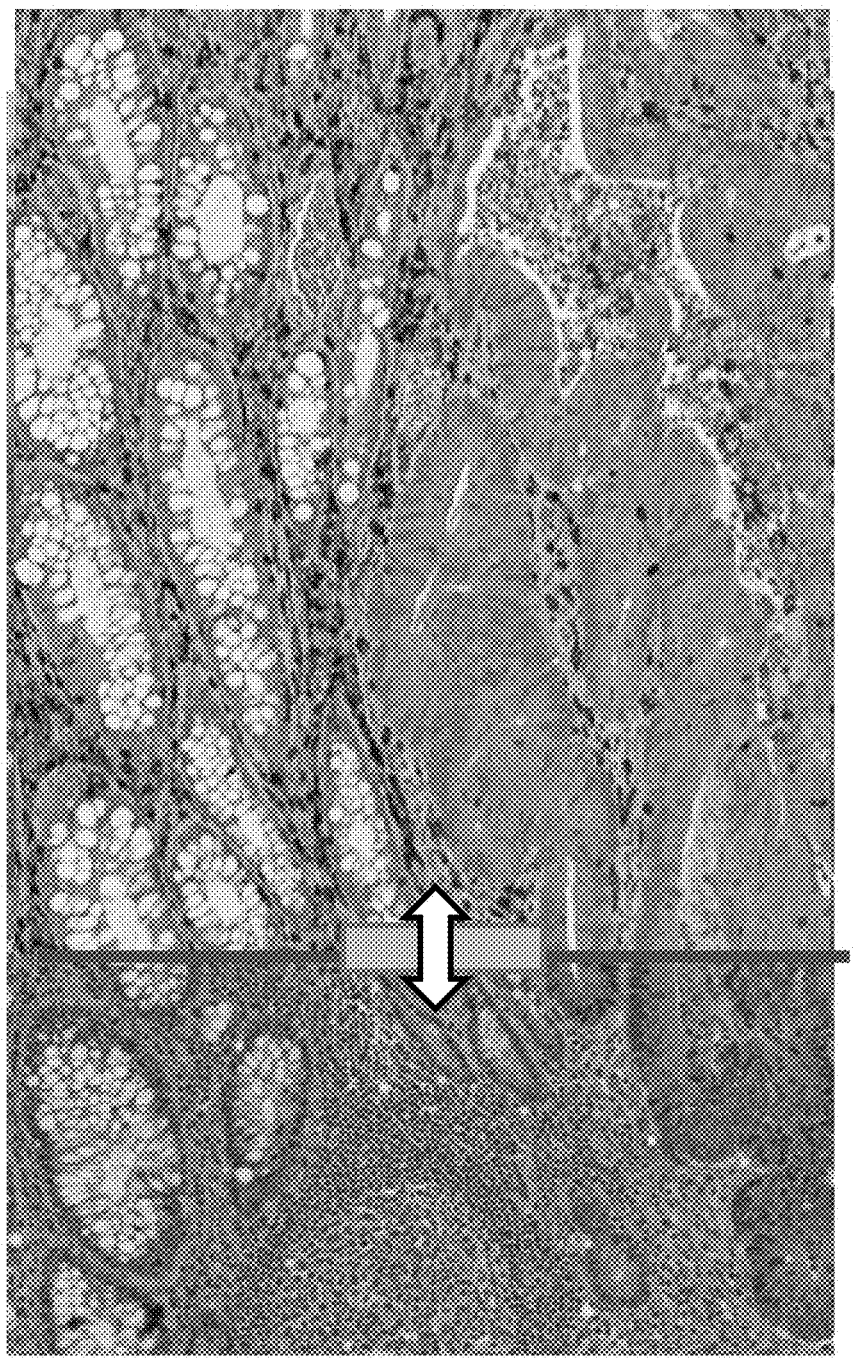
FIG. 9 is another screenshot of the screen of FIG. 8 after the boundary between different digital images has been moved again.

In curtain-view, as shown in FIG. 7, the selected slides appear stacked one on the other and a slider element can be dragged to determine what portion of the composite image is derived from one image versus another; that is, the slider button is moved to reveal a secondary, underlying image providing the appearance of a "curtain view" fused visualization. In the illustrated embodiment the digital image on the left side of the screen is derived from a slide of a tissue section stained with H&E, and the digital image on the right is derived from a slide of an adjacent tissue section stained with a IHC assay, for example, a duplex IHC assay. FIGS. 7-9 illustrate the appearance of the composite image as a result of moving the slider button from left to right. As can be seen, shifting the slider button shifts the proportion of each image's contribution to the composite image. In some embodiments, local registration adjusts at least one of the images so that the image data from the different slides is as similar as possible in the boundary area right and left of the curtain. Other viewer functionalities may also be used, including pan, zoom and creation of annotations.

Figure 10:
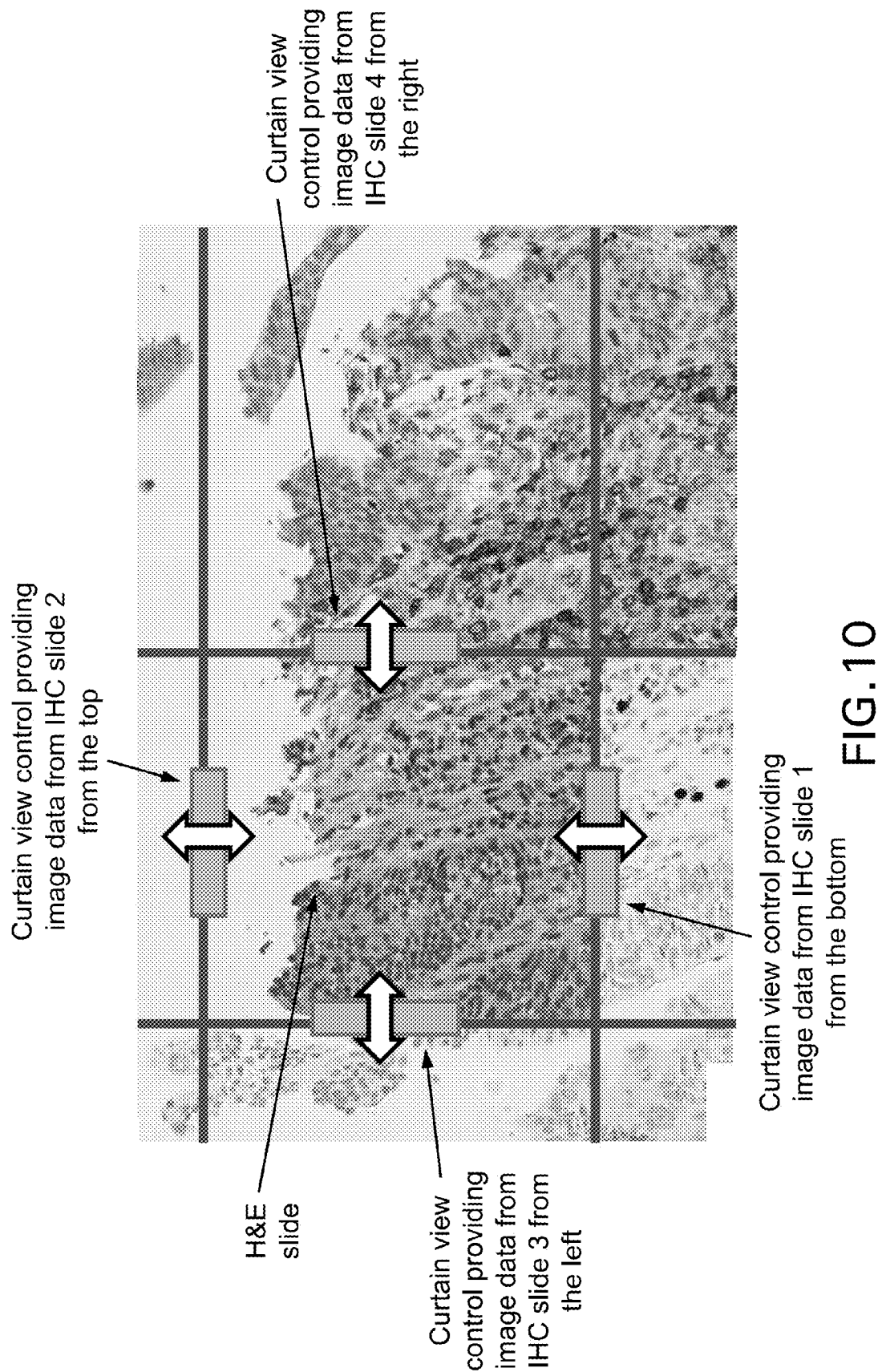
FIG. 10 is a screenshot another embodiment of the fused-view module GUI in which two or more digital slides may be viewed in a curtain-view composite image, and which may be launched from the home screen of FIG. 3.

As shown in FIG. 10, curtain view is not limited to a composite image of only two digital images of adjacent tissue sections and left-right movement of the slider button. In the example of FIG. 10, curtain view is applied to five slides and includes four slider buttons providing top to bottom, bottom to top, left to right and right to left control. In the illustrated curtain-view embodiment visualization, the central image is derived from an H&E stained slide with image data from digital images derived from IHC stained slides of adjacent tissue sections made visible (or invisible) with a respective curtain view (slider button) control.

Figure 11:
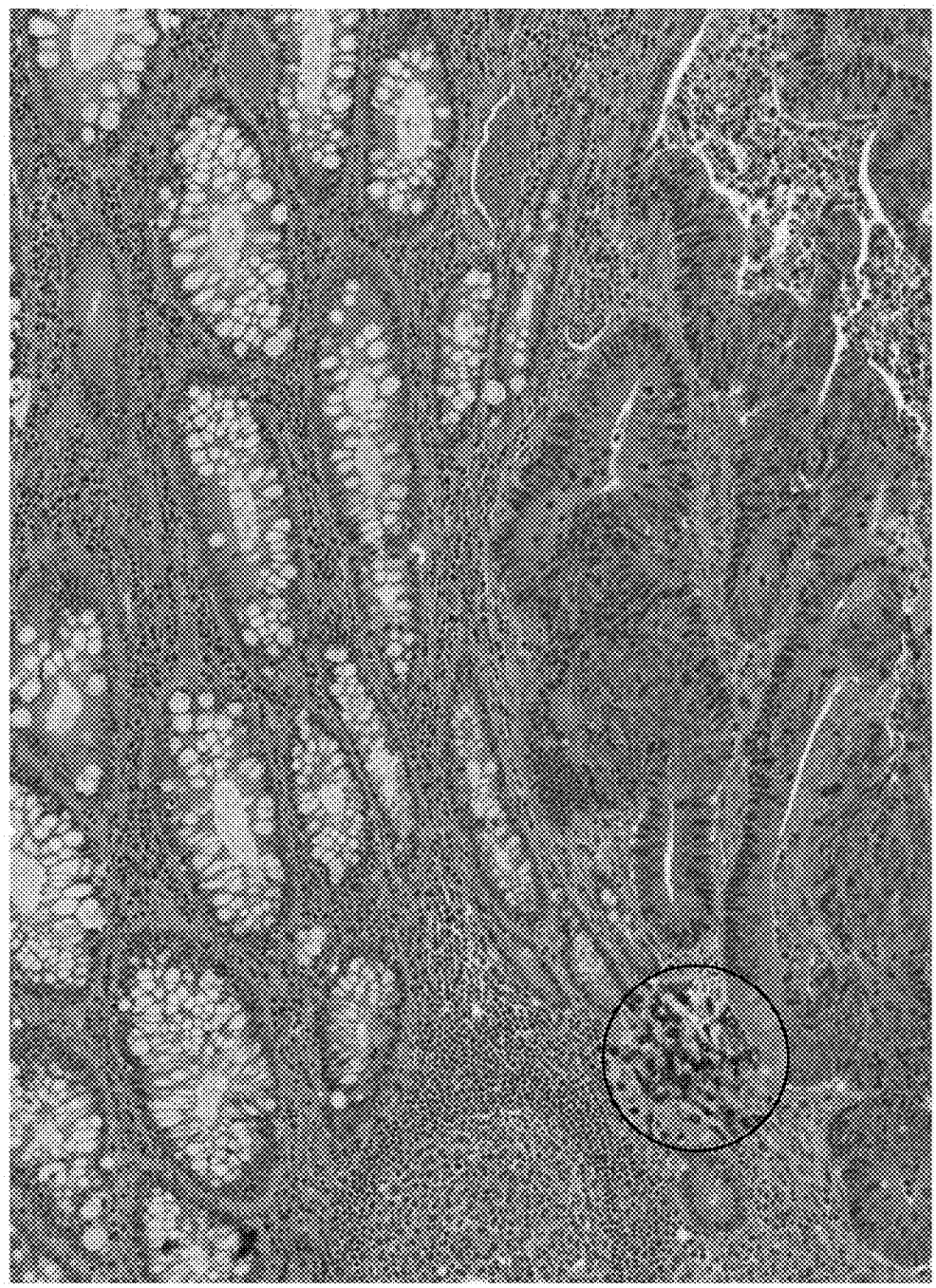
FIG. 11 is a screenshot of an embodiment of the fused-view module GUI in which two or more digital slides may be viewed in a flashlight composite image, and which may be launched from the home screen of FIG. 3.
Figure 12:
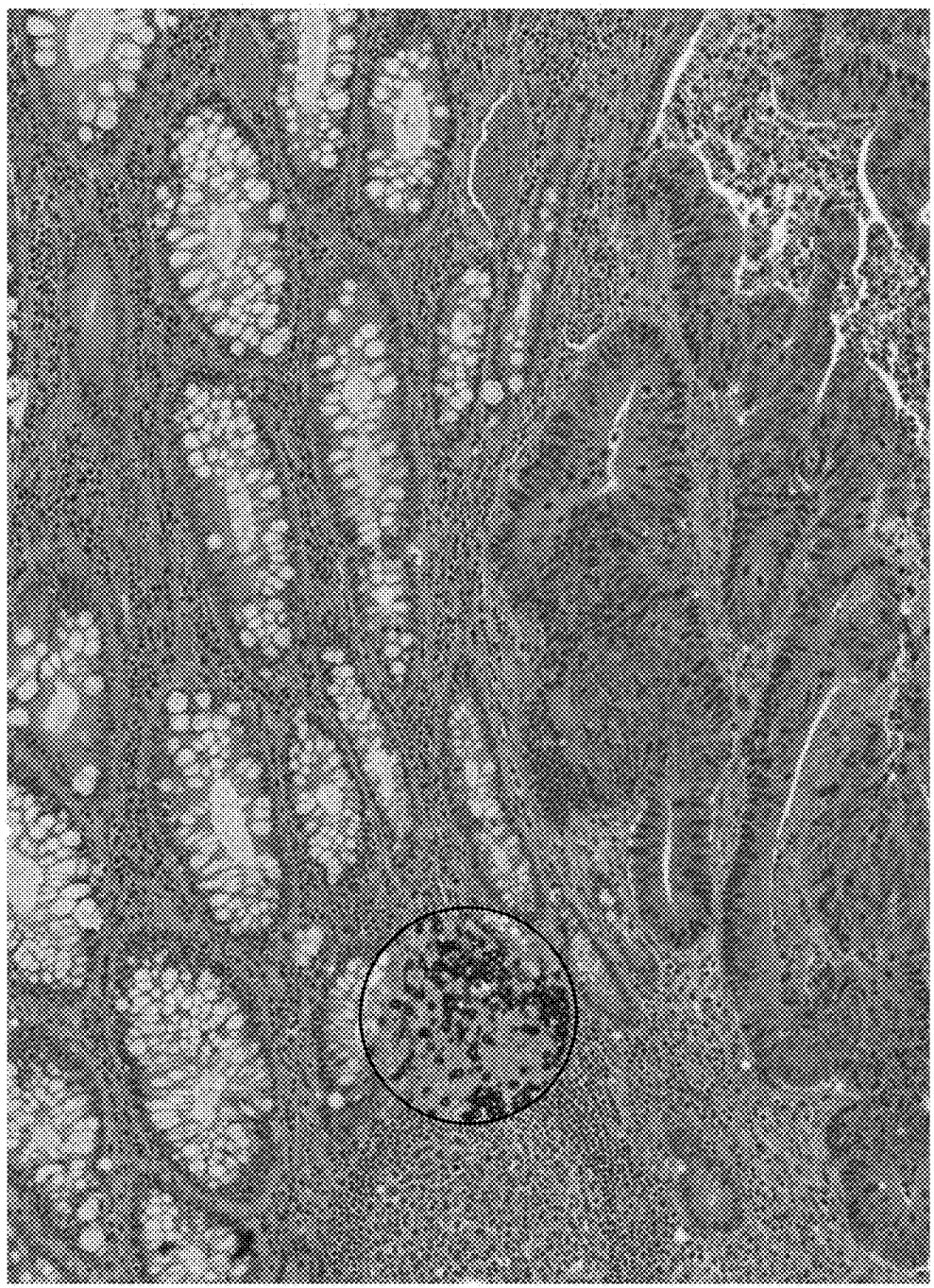
FIG. 12 is another screenshot of the fused-view module GUI of FIG. 11 after the boundary between different digital images has been moved.
Figure 13:
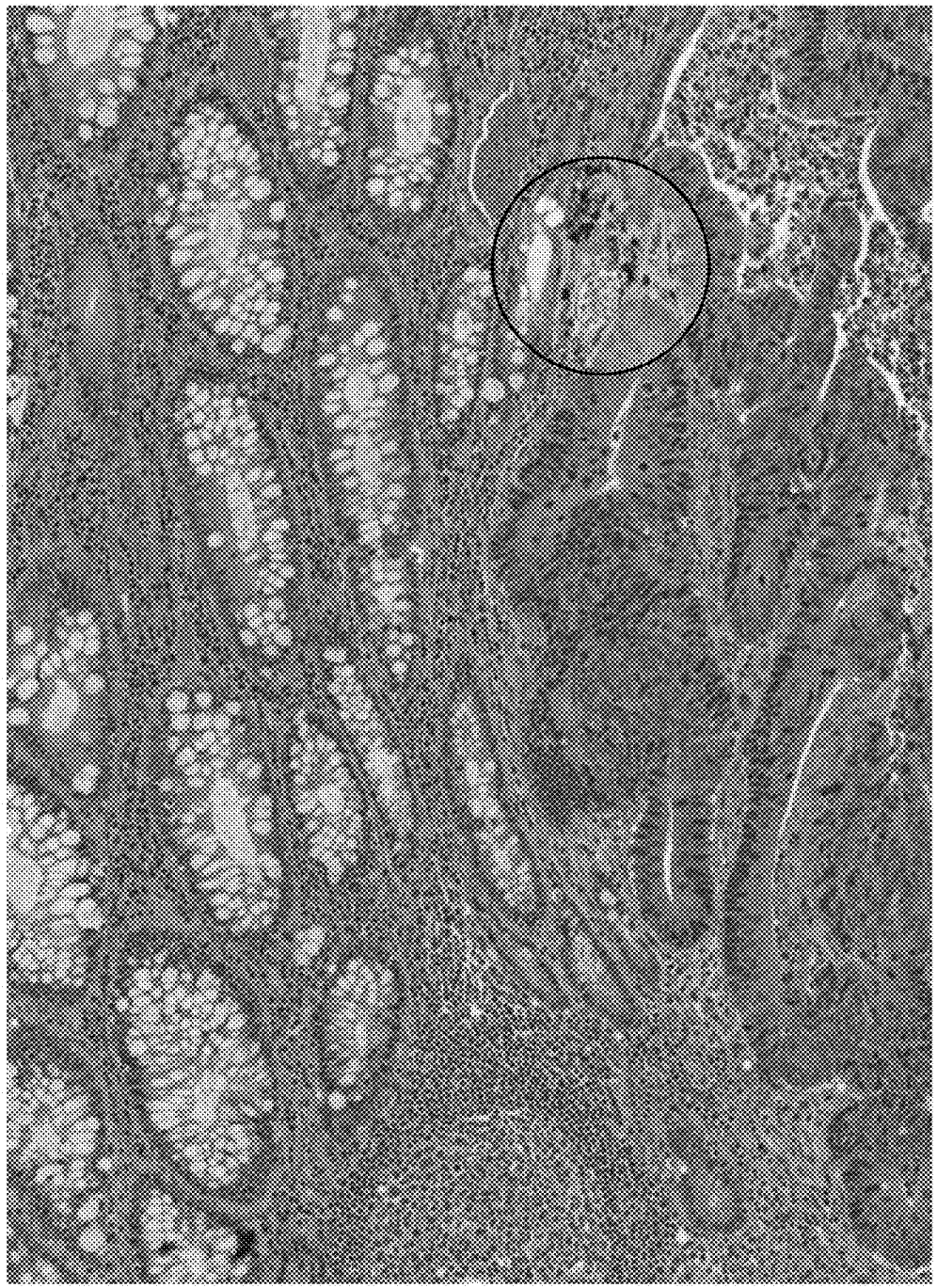
FIG. 13 is another screenshot of the fused-view module GUI of FIG. 11 after the boundary between different digital images has been moved.

Fusion viewing is not limited to the curtain view implementation but encompasses any manner in which a composite image may be visualized and/or manipulated. As an example, FIG. 11 illustrates another embodiment for fused viewing of two or more registered digital images of adjacent tissue sections of a sample: "flashlight" or "spotlight" fusion viewing wherein IHC data is overlaid on H&E data. Here, a user may select any region of a secondary image, which appears as if stacked under the primary (top) image, to replace corresponding image data of the primary image. In some implementations, the region from the secondary slide, which is fused-into the primary slide, is disc-shaped as if a flashlight or spotlight is shining on the replaced region. However the disclosure is not limited to disc-shapes. A user may further interact with the computer through the client user interface to increase or decrease the size of the region or modify the shape of the region. And, as shown in FIGS. 11-13, the user can shift the location of the region, for example by moving the mouse pointer (or any other interactive means such as voice control). Here again local registration may be used at the boundary between regions to adjust alignment between the regions.

Although the example of FIGS. 11-13 is of IHC data overlaid on H&E data, a user may also select which image is primary (top) and which is secondary (stacked/overlaid). Thus, for example, H&E data may be overlaid on IHC data. The ordering selection (that is, which image is assigned as primary and the layering of secondary, underlying images) can be made by the user at the time the images used for fused viewing are chosen. Alternatively, or in addition, the order of stacking can change during viewing, for example by reshuffling the stack (e.g. by instructing the top image to move to the back of the stack).

Further, although the example of FIGS. 11-13 illustrate only one fused (spotlight) region, in some embodiments there can be multiple fused regions. Each of the regions may provide image data from a single secondary slide, or else some or all of the regions may provide image data from different secondary slides.

FIG. 14 is a flow diagram illustrating an implementation of a method carried out by an embodiment of an image analysis software program in accordance with this disclosure. The image analysis software program enables a user to instruct the processor to view two or more images in fused view mode. In some embodiments, if the chosen images are not aligned, the program may also enable a user to register selected digital images (e.g. digital images of scanned slides of tissue sections, including whole slide images, partial slide images, or portions of whole or part slide images).

Figure 6:
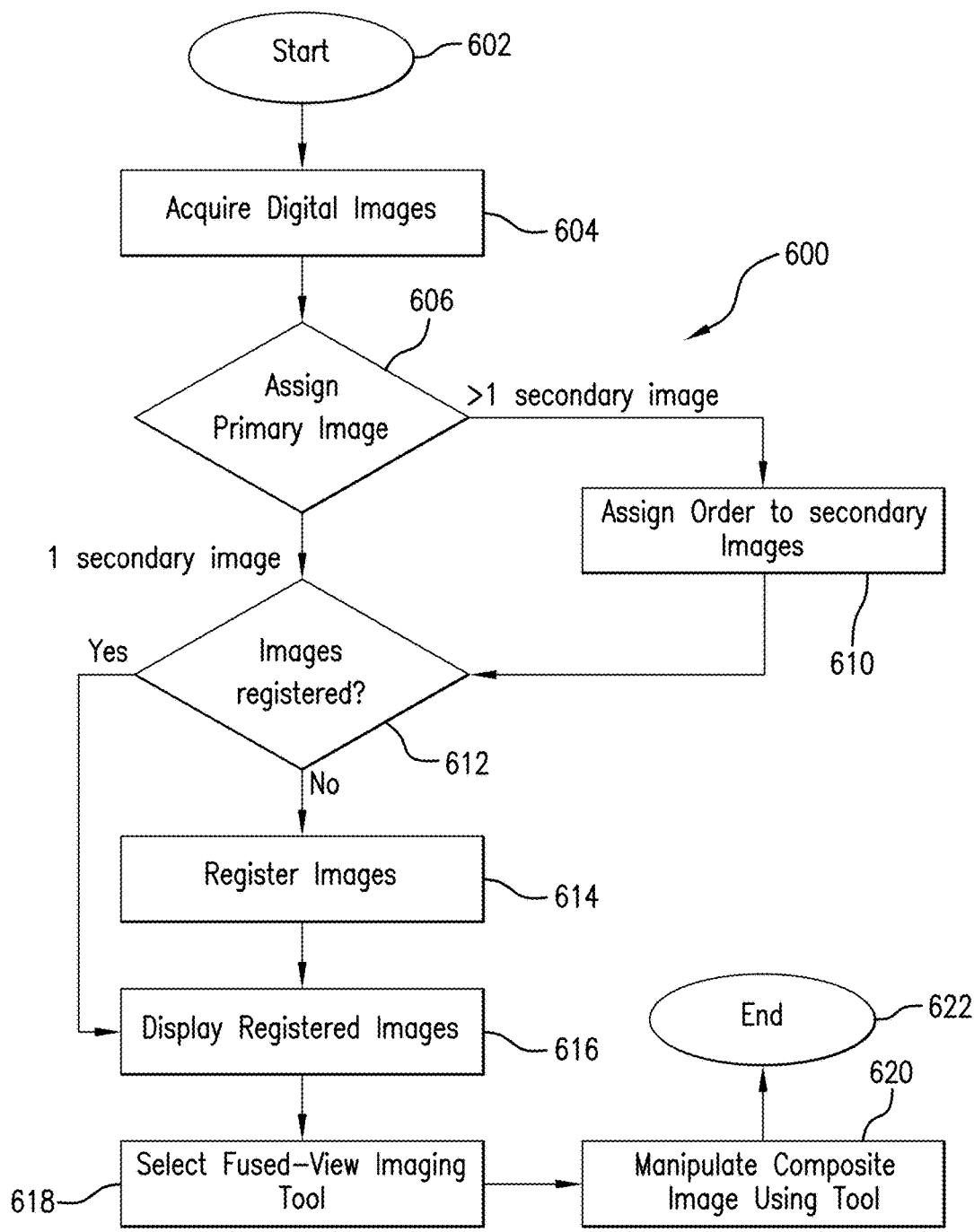
FIG. 6 is a flow diagram of an embodiment of a wholeslide viewer after the fused-view mode has been launched.

As shown in FIG. 6, the method 600 begins at the start block 602. At block 604, a set of image data or digital images is acquired (e.g. scanned or selected from the database or received from a source) for manipulation. Each set of image data includes image data corresponding to, for example, a tissue section from a set of adjacent tissue sections of a single patient. Each image may be derived from tissue sections that are differently stained, or that are digitized using a different imaging mode, or both, as compared to another image. In some embodiments, the digital images are produced by scanning slides (e.g. microscope glass slides) prepared from adjacent tissue sections.

At block 606, the user assigns an image among the selected images as the primary (i.e. top) image. If there is only one secondary image, then the procedure continues to block 612. Otherwise, at block 610, the user assigns an order to the secondary images.

Passing to block 612, if the selected images have previously been aligned, then the process proceeds to block 616. Otherwise, the images are aligned at block 614 using any image registration method. At block 616, the selected, and registered (aligned), images are displayed on a common grid, with the images overlaid in a single image and displayed on a monitor (or on several monitors). At block 618, the client user selects the fused view visualization tool such as curtain view, multiple curtain view, flashlight view, multiple flashlight view, resulting in the image being displayed as a composite image (with interactive features such as a slider button or spotlight), wherein information from the primary and one or more secondary digital images is combined such that different regions of the composite image show image data from different digital images, for example as described above in connection with curtain-view, multiple curtain-view, flashlight view and multiple flashlight view modes.

At block 620, the client user can interact with the display to manipulate the composite image to increase or decrease the proportion of image data being contributed by the primary and one or more secondary digital images. For example, in curtain view this may be accomplished by increasing the size of one curtain at the expense of another. As another example, in flashlight view this can be accomplished by one or more of increasing or decreasing the size of the spotlight and/or increasing or decreasing the number of spotlights.

In some embodiments, local registration occurs during this block 620 at the interface of two digital images when the interactive element (such as the slider or the spotlight) is activated (e.g., moved) to modify the composite image. Local registration is used to reduce alignment issues, which may occur at the boundary of two images that aren't identical but rather derive from adjacent tissue sections.

A client user may then decide either to end the procedure (proceed to block 622), or may decide to modify the composite image by modifying the selection of primary and secondary images. This can be done either by reordering the existing stack (to identify a new image as primary for example), or by selecting new (registered) images from the database and adding them to the stack or replacing existing images in the stack, partially or entirely, with the newly selected images. Again, if the images have been aligned, a new composite image is displayed, which can be manipulated using any of the fusion viewing tools. Or else, the images are first aligned, then displayed as a composite image ready for manipulation.

Certain embodiments have been described but a person of skill understands that still other embodiments are encompassed by this disclosure. It will be appreciated by those skilled in the art that changes could be made to the embodiments described above without departing from the broad inventive concepts thereof. For example, the disclosure is not limited to the fusion of two slides; multiple slides can be stained with different IHC and special stains assays, for example, and fused together for display. As another example, an H&E stained slide can be used with the IHC or other stained slides, but is not necessary. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention.

The invention claimed is:

1. A method comprising:
   obtaining two or more digital image files of adjacent tissue sections of a tissue sample;
   based on the two or more digital image files, providing for display a single output digital image comprising two or more regions, wherein each region has a size and shows image data from a different adjacent tissue section;
   obtaining a modification input from a user;
   responsive to the modification input, modifying the size of each region within the single output digital image and executing a local image registration process to match tissue structure along an interface between modified regions.

2. The method of claim 1, further comprising:
   selecting a first digital image from a set of digital images derived from slides of adjacent tissue sections of a single patient, wherein each slide is prepared using a different stain, a different imaging mode, or both as compared to other slides in the set;
   selecting one or more additional digital images from the set of digital images; and
   displaying the single output digital image as a composite of the first and one or more additional digital images.

3. The method of claim 2, wherein the stain is chosen from a hematoxylin and eosin stain ("H&E" stain) and an Immunohistochemistry stain ("MC" stain).

4. The method of claim 2, wherein the imaging mode is chosen from brightfield microscopy and fluorescent microscopy.

5. The method of claim 1, wherein different regions of the single output digital image show image data from different adjacent tissue sections in a side-by-side format.

6. The method of claim 5, wherein adjacent regions interface at an edge and the modification input comprises a movement of the edge.

7. The method of claim 5, wherein the single output digital image comprises five regions produced from a composite of five digital images of adjacent tissue sections and is displayed as a central square surrounded by four squares, one square adjacent each side of the central square.

8. The method of claim 5, wherein the different regions of the single output digital image show image data from different adjacent tissue sections in an overlaid format.

9. The method of claim 8, wherein the single output digital image comprises: a top layer derived from a first digital image of a first adjacent tissue section, which provides image data for a first region; and, a second layer derived from a second digital image of a second adjacent tissue section, which provides image data for a number of second regions, each of the number of second regions having a size and a shape.

10. An image analysis system, comprising:
    a. at least one processor; and
    b. at least one memory containing instructions which, when executed by the at least one processor, cause the system to perform operations comprising:
       i. displaying a digital composite image of a tissue section, wherein the digital composite image comprises two or more regions separated by and spatially aligned along a moveable boundary, wherein each region is derived from image data corresponding to a different slide in a set of slides of adjacent tissue sections, and
       ii. responsive to a user input, simultaneously modifying at least one of size and shape of the two or more regions, wherein modifying the at least one of size and shape of the two or more regions comprises performing a local image registration process, and
       iii. providing for display the digital composite image and a client user interface.

11. An image analysis system of claim 10, wherein the user input is provided through the client user interface and comprises a movement the moveable boundary.

12. The image analysis system of claim 10, wherein the composite digital image comprises regions in a spotlight display of one region within another region.

13. The image analysis system of claim 10, wherein the two or more regions are spatially aligned along the moveable boundary such that tissue structure displayed on one side of the moveable boundary corresponds to tissue structure displayed on the opposite side of the moveable boundary.

14. The image analysis system of claim 10, wherein the composite digital image comprises the one or more regions being displayed side by side and separated by the moveable boundary.

15. The image analysis system of claim 14, wherein modifying the at least one of size and shape of at least one of the regions comprises increasing the size of one region while decreasing the size of an adjacent region.

16. A non-transitory computer-readable storage medium storing instructions which, when executed by one or more processors of an image analysis system, cause the image analysis system to:
    a. produce and display an image of a tissue sample, which is a composite of one or more digital images in a set of digital images of adjacent tissue sections from the tissue sample, wherein each of the one or more digital images comprises a proportion of the composite image and each digital image in the set of digital images of adjacent tissue sections is obtained using a different stain, a different imaging mode, or both; and
    b. modify the proportion of one or more of the digital images in the composite image,
    wherein producing the composite image of the tissue sample and modifying the proportion of one or more digital images in the composite image comprises matching tissue structure at a boundary between digital images in the composite image.

17. A method for digitally viewing a tissue sample, comprising: a. selecting a first image from a set of digital images of adjacent tissue sections, wherein each image is produced from a slide obtained using a different stain, a different imaging mode, or both; b. selecting one or more second images from the set; c. aligning the selected first image and one or more second images under the first image to form an aligned layer of images; d. revealing a portion of one or more of the second images resulting in displaying a composite image of the tissue sample; e. modifying the revealed portion of the one or more images by moving a boundary displayed between adjacent images, and executing a local image registration process to match tissue structure along the boundary between adjacent images.

* * * * *